US00PP08790P

United States Patent [19]

Rudy et al.

[11] Patent Number: Plant 8,790

[45] Date of Patent: Jun. 21, 1994

[54] ACERACEAE DOLOROSA ET JEROMUS

[75] Inventors: Christopher J. Rudy, Minneapolis, Minn.; Michael J. Rudy, Sanford; Peter J. Rudy, Wyandotte, both of Mich.; Andrew J. Rudy, Washington, D.C.; Mark T. M. Rudy, Midland, Mich.

[73] Assignee: Dolores Rose Rudy, Midland, Mich.

[21] Appl. No.: 913,754

[22] Filed: Jul. 17, 1992

Related U.S. Application Data

[63] Continuation-in-part of Ser. No. 612,111, Nov. 13, 1990, abandoned.

[51] Int. Cl.[5] ..... A01H 5/00

[52] U.S. Cl. ..... Plt./53.6

[58] Field of Search ..... Plt. 51.1, 53.6

[56] References Cited

U.S. PATENT DOCUMENTS

| | | | |
|---|---|---|---|
| PP 2,139 | 4/1962 | Belcher | Plt./51 |
| PP 2,759 | 8/1967 | Schmidt, Jr. | Plt./51 |
| PP 3,060 | 8/1971 | Schmidt | Plt./51 |
| PP 4,392 | 3/1979 | Schmidt, III | Plt./51 |
| PP 7,222 | 4/1990 | Schmidt | Plt./51 |

OTHER PUBLICATIONS

Novak, "The Pictorial Encyclopedia of Plants and Flowers," Crown Publishers, Inc., New York, 1965, p. 367.

*Primary Examiner*—James R. Feyrer
*Assistant Examiner*—Bruce Campell
*Attorney, Agent, or Firm*—Chirstopher John Rudy

[57] ABSTRACT

A novel, apparent interspecific hybrid maple tree differs in characteristics from common maple tree species. These include in having a growth habit characterized by a substantially straight hole formed which conspicuously is an unbranched central leader, scaffold branches which are generally directed and exceedingly narrow when compared to those of other maple species, and attractive foliage which is unusually cut and which is not of the usual contrast in coloration and texture from to bottom surfaces. Also, the new tree is a seedless variety.

3 Drawing Sheets

CROSS REFERENCE TO RELATED APPLICATION

This is, in accordance with Rule 62, a continuation-in-part of U.S. patent application Ser. No. 07/612,111 which was filed on Nov. 13, 1990 and abandoned in favor hereof.

BACKGROUND OF THE INVENTION

1. Field of the Invention

The present invention concerns a new and distinct maple tree. The tree was discovered in a cultivated area. It was discovered at 3613 Orchard Drive, Midland, Mich.

The new tree may be propagated asexually by budding on a suitable other maple tree. Such budding is well known in the art. See e.g., U.S. Plant Pat. Nos. 4,392 (Mar. 6, 1979); 3,060 (Aug. 10, 1971); 2,759 (Aug. 15, 1967); 2,139 (Apr. 24, 1962), each incorporated herein by reference. In addition, the new tree may be propagated asexually by grafting, for example, a bud or scion into a root portion of the new tree. A section of its root may be lifted above ground to expose it to air and light. Other methods may be employed, e.g., known mist rooting, hormone-assisted rooting, etc.

The new tree has been asexually reproduced by division. Shoots growing near the base of the tree were cut away from the parent tree while keeping the shoots attached to a root section.

The new tree has been established as stable. The phenotype of the claimed plant is stable, i.e., the asexually reproduced offspring retain the distinguishing characteristics of the parent plant.

2. Description of the Related Art Including Information Disclosed Under Rules 56 & 97-99 Especially Under Current Rules 56, 97 & 98

The important Maple family, Aceraceae, formerly has been known to include about 120 species, all but two of which being belong to the genus Acer. In general, they are North temperate trees or shrubs with opposite leaves and small flowers, and fruit consists of two one-seeded portions. Source: Novak, "The pictorial Encyclopedia of Plants and Flowers," Crown Publishers, Inc., New York 1965, page 367.

Belcher, U.S. Plant Pat. No. 2,139 (Apr. 24, 1962), discloses a Maple Tree, believed a variety of the sugar maple tree.

Schmidt, Jr., U.S. Plant Pat. No. 2,759 (Aug. 15, 1967), discloses a Norway Maple Tree, believed a variety of the Norway maple species.

Schmidt, U.S. Plant No. 3,060 (Aug. 10, 1971), discloses a Maple Tree, a sport of unknown parentage of the Norway maple species.

Schmidt, III, U.S. Plant Pat. No. 4,392 (Mar. 6, 1979), discloses a Maple Tree, a distinct variety of maple tree commonly called "Hedge Maple."

Schmidt, U.S. Plant Pat. 7,222 (Apr. 24, 1990), discloses a Magnificent Magenta Maple, a unique variety of the red or swamp maple species.

Seedless Silver Maple, a variety commercially available in Michigan, is similar to the present invention in some characteristics, such as leaf morphology.

The silver maple is a common North American maple with deeply cut leaves that are light green above and silvery white below.

The miniature Japanese cutleaf maple is an ornamental variety with ornate, deeply cut leaves that are commonly violet.

SUMMARY OF THE INVENTION

The new tree is believed to have characteristics as of silver maple and miniature Japanese cutleaf maple trees, although its parentage is unknown. In general, the following is further noted:

Primary distinguishing characteristics of the new tree include the unusual form in combination with color of its leaves, its attractive foliage, its trunk and its branching, and the rate and style of its growth. The leaves are deeply cleft with many fine serrations on the edges of their elongate lobes; in summer, they are typically green, and in fall, typically yellow; however, color may vary, even among leaves of the same tree; the top and buttom surfaces of the leaves are believed to be not exceedingly widely contrasting in surface aspect or coloration. The foliage is airy and open. The new tree has a remarkable growth habit with an unusually straight bole formed, and scaffold branches are generally laterally directed and unusually narrow in comparison to the bole as compared to those of other species within Acer per se. It grows more slowly than the common silver yet more greatly than the miniature Japanese cutleaf maple trees. A comparison of the present invention with the Silver Seedless, believed to be the most similar cutivated variety, is presented as follows:

| | Seedless Silver | Tree of this Invention |
|---|---|---|
| LEAVES | Blades darker green | Blades lighter green |
| | Less fine, frilly cuts | More fine, frilly cuts |
| | Deeper central clefts | More shallow central clefts |
| | Deeper outside clefts | More shallow outside clefts |
| | Less blade near petiole | More blade near petiole |
| | Petioles white | Petioles red cast |
| | Veins more pronounced | Veins less pronounced |
| BRANCHES | More acutely angled to bole | Less acutely angled to bole |
| | Vertically directed growth | Horizontally directed growth |
| | Orange cast when young | Brown/grey cast |
| | Very smooth, shiny bark | More rough, matte bark |
| | Leaves far apart on branches | Leaves closer on stems. |

BRIEF DESCRIPTION OF THE DRAWINGS

The new tree is further illustrated by the accompanying drawings, part of the specification hereof, in which.

BOTANICAL DESCRIPTION OF THE TREE

Figure 1A:
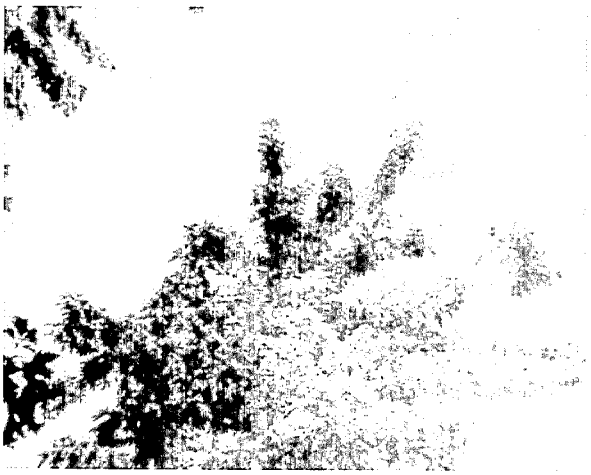
FIG. 1 is a composite picture of the new tree, to show it in three overlapping sections, 1A, 1B, 1C, taken of the top of its crown, a middle section of its crown, and a lower section of its crown down to a level substantially above ground, respectively, in its summer display at 3613 Orchard Drive, Midland, Mich.

The tree has never been observed to flower. Male flowers have bloomed at bases of some leaf buds alone or in oppositely positioned pairs. Each flower contains five cuplike florets (-150D yellow-green) about 4 to 5 mm in height with fluted mouth tips (-180C greyed-red) about 1 to 2 mm in diameter, arranged upright in an orthogonal cruciform pattern with one of the five being central. Each floret has about 4 or 5 stamens, with filaments thrust about 7 to 10 mm beyond the floret mouth and oval anthers approximately 1 by 0.5 mm. Sepals oppose one another in four pairs, with each pair orthogonal the next. An innermost pair of sepals (-180D grayed-red and -150D yellow-green) are dominant in size, with the next pair (-180A-C grayed-red) less dominant in size outside the innermost pair, and so on with the remaining two pairs of sepals. Sepal pairs are centrally aligned on axes of the upright florets. The tree bloomed at the same time as nearby female Silver Maple trees. Seed formation has not been noted.

The growth habit of the new tree is quite unusual for maples in that a clear central leader is formed and in that there is a conspicuous absence of major scaffold branches. Crotch angles of connecting branches to the generally vertically upright trunk appear to be strong and typically between about 30 to 90 degrees or so, often of about 45 degrees or so, from the trunk, but branches appear to extend laterally from the trunk and parallel to the ground or to take on a slight weeping appearance due to branch length relative to girth, weight of foliage, etc. Otherwise in general, the trunk of the new tree resembled that of a silver maple more than that of said miniature cutleaf tree. However, the branches of the new tree have distinct characteristics in resemblance to the branches of said cut leaf tree, which open well and retain a nice, ornamental appearance. The ultimate tree shape generally appears as a vertically elongate oval or ellipsoidal when viewed from the side on the ground.

The new tree has some propensity to form surface roots.

Characteristic vigor of the new tree includes that terminal growth of twigs is about from one-half and inch to an inch annually on elder specimens of the branches. The new tree grows more slowly than the silver maple; it is of moderate sensitivity to crowding by other trees, particularly growing away from such crowding. However, the new tree can attain a fairly good height, for example, growing to about twenty-five or so feet in a score (twenty) or so years, to include growth after transplanting the same as a young sapling.

Coloration of the new tree generally resembles the silver maple. Of course, actual coloration may vary with environment to include soil and weather conditions.

The following two tables illustrate some coloration noted for the tree of the invention:

GENERAL, AS OBSERVED UNAIDED, COLORATION TABLE

| New Tree Part | Typical Coloration Scheme and Comment |
|---|---|
| Spring Leaves | Fresh green, generally as silver maple |
| Mature Leaves | Green, generally as silver maple, occasional leaves tinged red |
| Autumn Leaves | Bright yellow, generally as silver maple, some tinged red |
| Petioles | Yellow-green to red |
| Winter Buds | A bright red hue |
| Branch Bark | Dark brown |
| Trunk Bark | Lighter grey with dark brown at branches and lenticels. |
| Roots | Some, especially some smaller ones, reddish-orange cast |

R.H.S. COLOUR CHART COLORATION TABLE (APPROXIMATE)

| New Tree Part | R.H.S. Color as Determined by Employing Flower Council of Holland Fans and Dry Tree Parts |
|---|---|
| Spring Leaves | Top: Yellow-green 144A-B (late spring)<br>Bottom: Greyed-green 191B (late spring) |
| Summer Leaves | Top: Yellow-green 144A with occasional green 143A<br>Bottom: Greyed-green 191B |
| Autumn Leaves | Top: Yellow 11A with some green, red, brown speckling<br>Bottom: Greyed-yellow 161D |
| Buds | Red-purple 60B |
| Bark | Greyed-green 198A with areas of possible aphid residue of black 202. |

The leaves may appear, however, at least as appears in some photographs, to be colored top and bottom to a degree that generally resembles one another. There are typically five leaf lobes, with the central three of these being major in size. The lobes are deeply cut; along the three major lobes, pairs of opposing clefts appear, and the edges of each of the five lobes are finally serrated, which would seem to resemble more the fashion of said cutleaf leaves, but not, however, their size. The leaves of the new tree may vary in size, but are typically about from two to four or more inches in length. This length is measured from the leaf base to the leaf tip, but does no include the leaf stem (petiole). For the most part, leaves of the new tree span less in their width than in their length, and have a petiole to leaf ratio of less than one. Each leaf is open and airy. Also, overall, the foliage of the new tree appears fairly airy and light. In general, the relative dates of foliation and leaf fall are as follows: In the spring, the new tree shoots its leaves about the same time as other maples in the same area if not later, and in the fall, the new tree sheds it leaves about the same time as other maples in the area if not earlier.

The winter buds of the new maple are fairly small, and they appear often as solitary major buds at the end of a stem. Major terminal buds are typically of a pointed oval shape, each somewhat like a little red bullet, but numerous tiny buds may accompany the major terminal bud along the stem near the major bud.

The bark along the trunk is relatively, generally smooth for a tree trunk, except near the junctions of the branches and lenticels. It is not smooth to the point of being shiny, but it has a matte appearance. The bark along the branches is generally rougher if not bumpy or segmented in appearance near ends of the branches.

CONCLUSION

The new tree is believed to be particularly useful in landscaping, providing a new, nicely-sized tree with a clean, ornamental and nicely airy appearance, with intriguing leaves and good summer and fall colorations, and branching which is appealing to the eye. The new tree seems quite durable.

Clearly as well, the narrow branching of the new tree in conjunction with its generally straight, upright trunk might also provide for a maple useful in wood products. Veneers might be of particular possible interest in this regard.

The new tree is named after our parents.

We claim:

1. A new and distinct variety of maple tree, Aceraceae "Dolorosa et Jeromus," as depicted, described and illustrated herein.

* * * * *

UNITED STATES PATENT AND TRADEMARK OFFICE

CERTIFICATE OF CORRECTION

PATENT NO. : Plant 8,790

DATED : June 21, 1994

INVENTOR(S) : Rudy Bros.

Figure 1B:
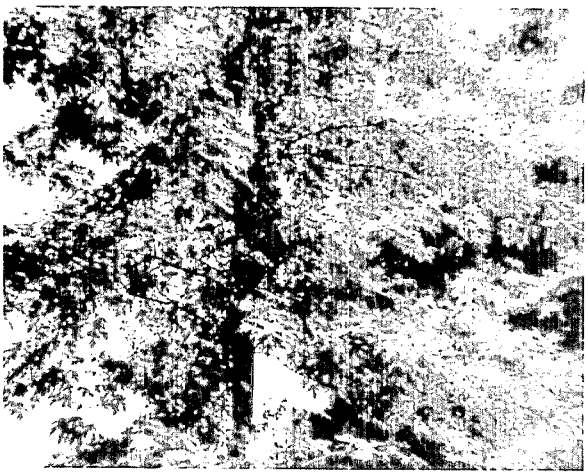
Figure 1C:
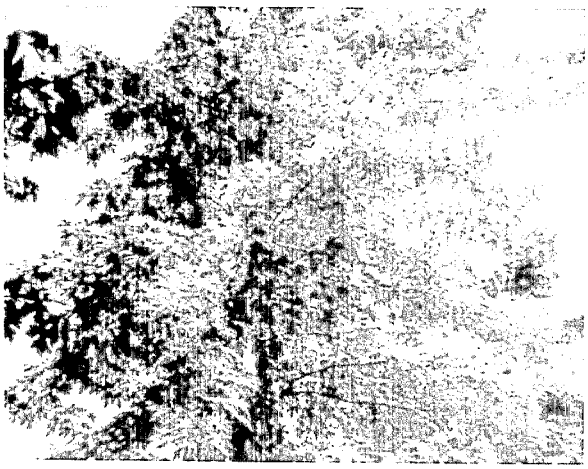
Figure 2:
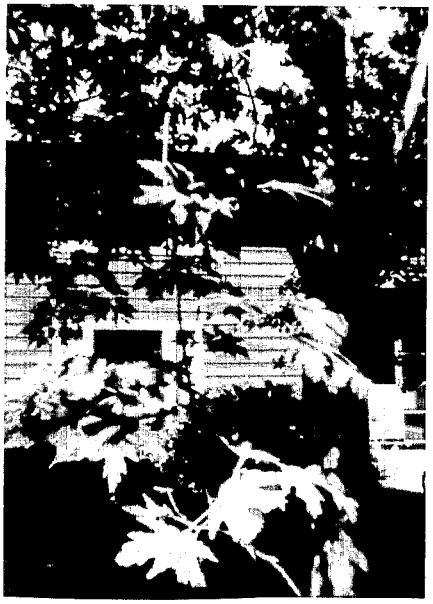
FIG. 2 is a picture of the same tree showing its trunk, lower branching, and foliage in summer display at a height about six or so feet above ground, which shows some red tinged leaves as well.
Figure 3:
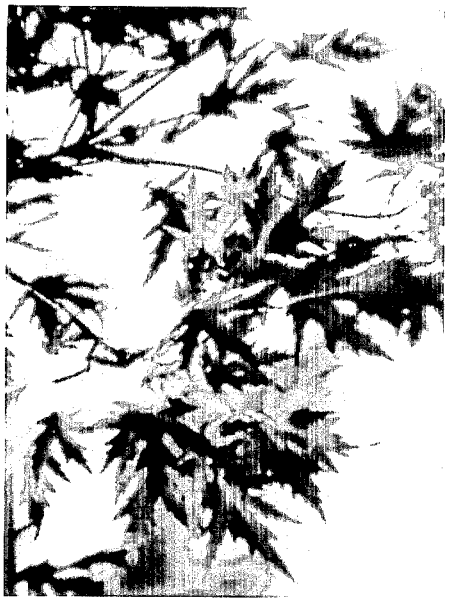
FIG. 3 is a picture of the same tree showing some of its leaves in their summer display casting shadows on a white sheet.
Figure 4:
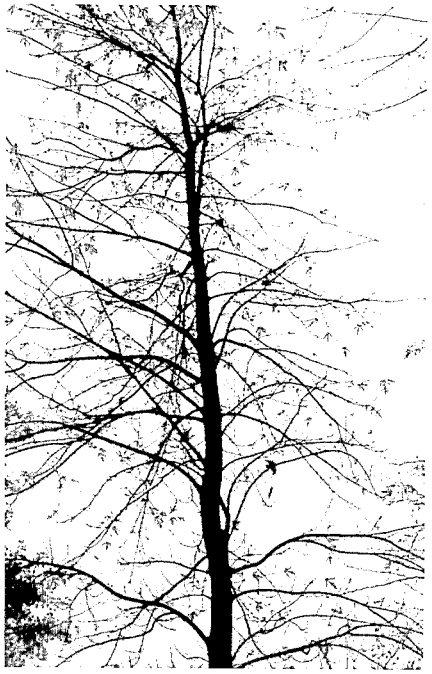
FIG. 4 is a picture of the same tree showing an upper portion of its trunk, accompanying branches, and some of its leaves remaining thereon in their fall display.
Figure 5:
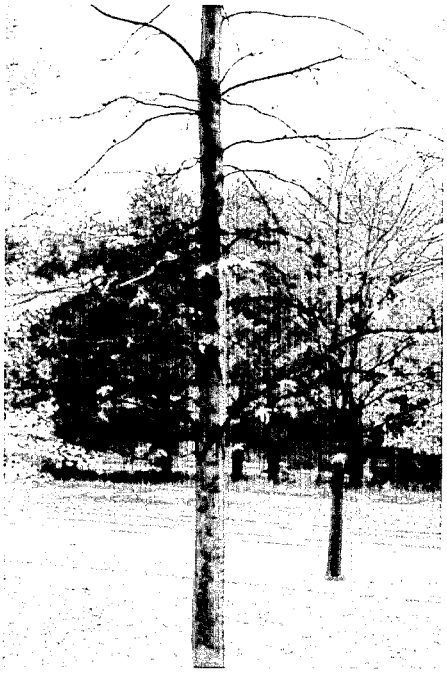
FIG. 5 is a picture of the same tree showing a lower portion of its trunk, accompanying branches, and some of its leaves remaining thereon in their fall display.
Figure 6:
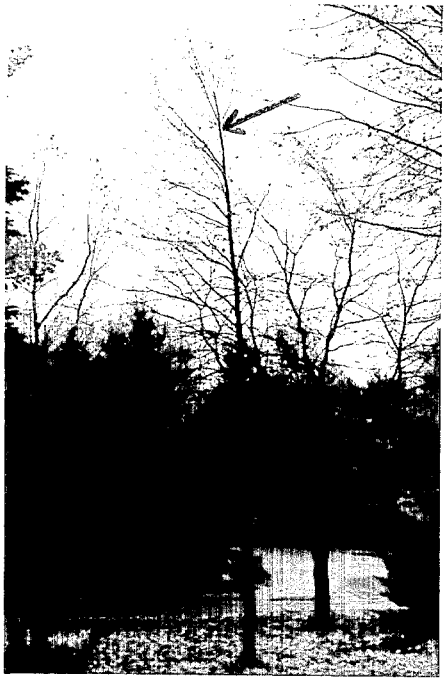
FIG. 6 is a picture of the same tree showing its whole trunk, accompanying branches, and some of its leaves remaining thereon in their fall display.
Figure 7:
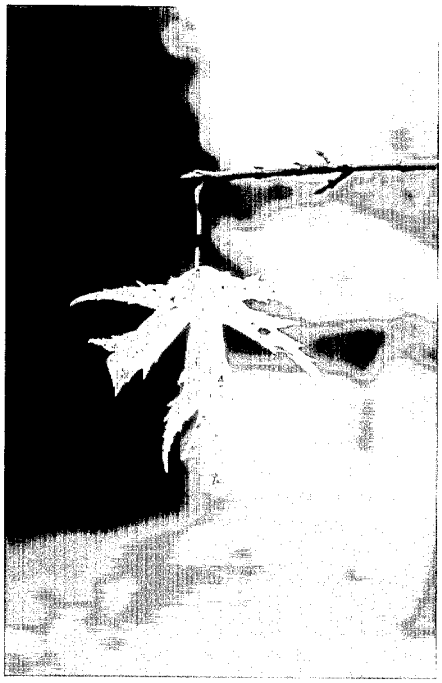
FIG. 7 is a picture of a leaf on the same tree in its fall display with some accompanying buds.
Figure 8:
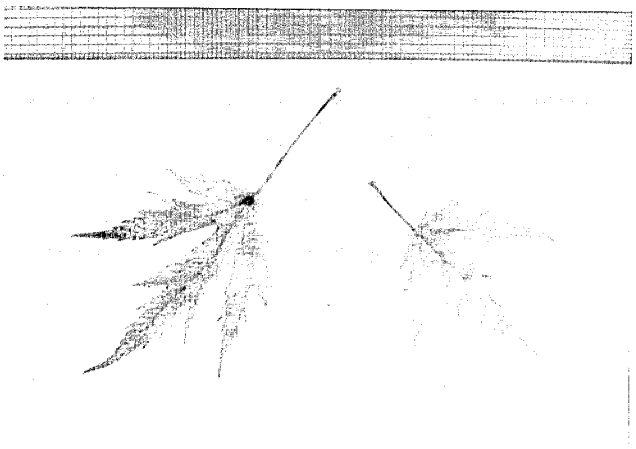
FIG. 8 is a picture of two leaves from the same tree in their fall display resting on a white paper sheet with a scale in inches thereon.

It is certified that error appears in the above-indentified patent and that said Letters Patent is hereby corrected as shown below:

In the Drawings, delete "Fig. 1B" and insert -- Fig. 1C -- and also delete "Fig. 1C" and insert -- Fig. 1B --.

On the title page: Attorney, Agent or Firm should read as follows -- Christopher John Rudy --.

In the Abstract, line 4, delete "hole" and insert -- bole --, and line 6, directly after "generally" insert -- laterally --.

At col. 4, line 12, delete "never" entirely.

At col. 4, line 42, delete "resembled" and insert -- resembles --.

At col. 4, line 53, delete "and" and insert -- an --.

At col. 6, line 1, delete "no" and insert -- not --.

Signed and Sealed this

Thirty-first Day of January, 1995

*Attest:*

Bruce Lehman

BRUCE LEHMAN

*Attesting Officer*

*Commissioner of Patents and Trademarks*